(12) United States Patent
Sato et al.

(10) Patent No.: US 12,004,738 B2
(45) Date of Patent: Jun. 11, 2024

(54) NEEDLE HOLDER AND METHOD OF USING SAME

(71) Applicant: OLYMPUS CORPORATION, Hachioji (JP)

(72) Inventors: Masatoshi Sato, Tokyo (JP); Hiroyuki Morishita, Tokyo (JP); Keisei Shimoda, Tokyo (JP); Takayuki Hatanaka, Hirosaki (JP); Masaya Ota, Yokohama (JP); Kei Matsuoka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 696 days.

(21) Appl. No.: 17/022,944

(22) Filed: Sep. 16, 2020

(65) Prior Publication Data

US 2020/0405289 A1    Dec. 31, 2020

Related U.S. Application Data

(63) Continuation of application No. PCT/JP2018/011352, filed on Mar. 22, 2018.

(51) Int. Cl.
*A61B 17/062* (2006.01)
*A61B 17/00* (2006.01)
*A61B 17/06* (2006.01)

(52) U.S. Cl.
CPC .. *A61B 17/062* (2013.01); *A61B 2017/00296* (2013.01); *A61B 2017/0608* (2013.01)

(58) Field of Classification Search
CPC .............. A61B 17/062; A61B 17/0625; A61B 17/06061; A61B 2017/00296;

(Continued)

(56) References Cited

U.S. PATENT DOCUMENTS

| 5,951,587 | A |  | 9/1999 | Qureshi et al. |
| 8,282,669 | B2 | * | 10/2012 | Gerber ............... A61B 17/0483 |
|  |  |  |  | 606/205 |
| 2005/0096694 | A1 | * | 5/2005 | Lee ..................... A61B 17/062 |
|  |  |  |  | 606/205 |

FOREIGN PATENT DOCUMENTS

| JP |  | 6197151 B1 | 9/2017 |
| WO |  | 2017/145337 A1 | 8/2017 |

OTHER PUBLICATIONS

May 15, 2018 International Search Report issued in International Patent Application No. PCT/JP2018/011352.

* cited by examiner

*Primary Examiner* — Katherine M Shi
*Assistant Examiner* — Mohammed S Adam
(74) *Attorney, Agent, or Firm* — Oliff PLC

(57) ABSTRACT

A needle holder for holding a curved needle to which a suture thread is connected. The needle holder includes a flexible tube; and a grasper provided at a distal end of the flexible tube. The grasper includes a first jaw having a groove, and a protrusion at a distal end portion of the first jaw; and a second jaw movably connected to the first jaw. The grasper can hold the curved needle between the second jaw and the protrusion of the first jaw, and can hold a part of the suture thread between a surface of the groove and the second jaw such that another part of the suture thread passes through a gap formed between another surface of the groove and the second jaw. The protrusion has a hook surface for hooking the suture thread extending outside the groove.

19 Claims, 13 Drawing Sheets

(58) Field of Classification Search
CPC .. A61B 2017/0608; A61B 2017/06052; A61B 17/28; A61B 17/29; A61B 17/282
See application file for complete search history.

NEEDLE HOLDER AND METHOD OF USING SAME

This application is a continuation application of a PCT International Application No. PCT/JP2018/011352, filed on Mar. 22, 2018. The contents of the PCT International Application are incorporated herein by reference.

BACKGROUND

Conventionally, surgical procedures of using a curved needle and a suture thread to suture the tissues in a body are known. For example, a needle holder can be inserted into a channel of a flexible endoscope to be used. The needle holder disclosed can be designed to hold a curved needle connected to the suture thread by a pair of grasping members.

SUMMARY

The present disclosure relates to a needle holder and a method of using the needle holder.

One aspect of the present disclosure provides a needle holder for holding a curved needle to which a suture thread is connected. The needle holder includes a flexible tube; and a grasper provided at a distal end of the flexible tube. The grasper includes a first jaw including a groove extending along a longitudinal axis and a protrusion provided at a distal end portion of the first jaw; and a second jaw movably connected to the first jaw. The grasper can hold the curved needle between the second jaw and the protrusion, and can hold a part of the suture thread between a surface of the groove of the first jaw and the second jaw such that another part of the suture thread passes through a gap formed between another surface of the groove and the second jaw. The protrusion has a hook surface for hooking the suture thread extending outside the groove.

In other aspects, the groove of the first jaw may have a bottom surface facing a grasping surface as part of an outer circumferential surface of the second jaw when the second jaw is closed with respect to the first jaw; and a lateral surface intersecting to the bottom surface and being formed to extend between the bottom surface and an edge of the groove, wherein the first jaw has a curved-needle pressing portion provided at the edge of the groove of the first jaw, wherein the curved-needle pressing portion is configured to press the curved needle together with the outer circumferential surface and the protrusion of the second jaw at the time of pressing and holding the curved needle, wherein when the part of the suture thread is pressed and held by the bottom surface of the groove and the grasping surface, part of the suture thread continuing to one end of the part of the suture thread is freely moveable in the gap formed between the lateral surface of the groove and the outer circumferential surface of the second jaw.

In further aspects, the groove of the first jaw may have a second lateral surface intersecting to the bottom surface and facing the lateral surface, and the needle holder may be configured to hold a second part of the suture thread continuing to the other end of the part of the suture thread in a second gap formed between the second lateral surface of the groove and the outer circumferential surface of the second jaw.

In yet further aspects, the first jaw may have an outer edge surface continuing to the edge of the groove and extending to intersect with the lateral surface, the protrusion may protrude from a distal end of the outer edge surface in a direction intersecting to the outer edge surface, and the curved-needle pressing portion may be positioned at a boundary between the outer edge surface and the lateral surface.

In another aspect, a dimension of the gap may be larger than a diameter of the suture thread.

In another aspect, the bottom surface may be substantially parallel to the grasping surface in a state when the part of the suture thread is held by the bottom surface of the groove and the grasping surface.

Another aspect relates to a method of operating a needle holder together with an endoscope. The needle holder includes a flexible tube; and a grasper provided at a distal end of the flexible tube. The grasper includes a first jaw having a groove extending along a longitudinal axis, and a protrusion provided at a distal end portion of the first jaw; and a second jaw movably connected to the first jaw. The method includes holding a curved needle between the first jaw and the second jaw in a state when the first jaw and the second jaw are protruded from a distal end of the endoscope; holding a suture thread connected to the curved needle between the first jaw and the second jaw while maintaining the state when the first jaw and the second jaw are protruded from the distal end of the endoscope, and hooking the suture thread extending outside the groove to the protrusion in the state when a part of the suture thread is pressed and held by the first jaw and the second jaw.

In other aspect, the groove of the first jaw may have a bottom surface facing a grasping surface as part of an outer circumferential surface of the second jaw when the second jaw is closed with respect to the first jaw; and a lateral surface intersecting to the bottom surface and being formed to extend between the bottom surface and an edge of the groove, in the step of holding the curved needle, the curved needle may be pressed and held by the outer circumferential surface of the second jaw, the edge of the groove, and the protrusion, and in the step of holding the suture needle, when the part of the suture thread is pressed and held by the bottom surface and the grasping surface, part of the suture thread continuing to one end of the part of the suture thread may be held to be freely moveable in a gap formed between the lateral surface of the groove and the outer circumferential surface of the second jaw.

In another aspect, the groove of the first jaw may have a second lateral surface intersecting to the bottom surface and facing the lateral surface, and a second part of the suture thread continuing to the other end of the part of the suture thread may be held in a second gap formed between the second lateral surface of the groove and the outer circumferential surface of the second jaw.

According to another aspect, the first jaw may have an outer edge surface continuing to the edge of the groove and extending to intersect with the lateral surface, and the protrusion may protrude from a distal end of the outer edge surface in a direction intersecting to the outer edge surface.

According to another aspect, a dimension of the gap may be larger than a diameter of the suture thread.

According to another aspect, the bottom surface may be substantially parallel to the grasping surface in a state when the part of the suture thread is held by the bottom surface and the grasping surface.

DETAILED DESCRIPTION OF EMBODIMENTS

Hereinafter, an exemplary embodiment of the present disclosure will be described by referring to FIG. 1 to FIG. 14.

Figure 1:
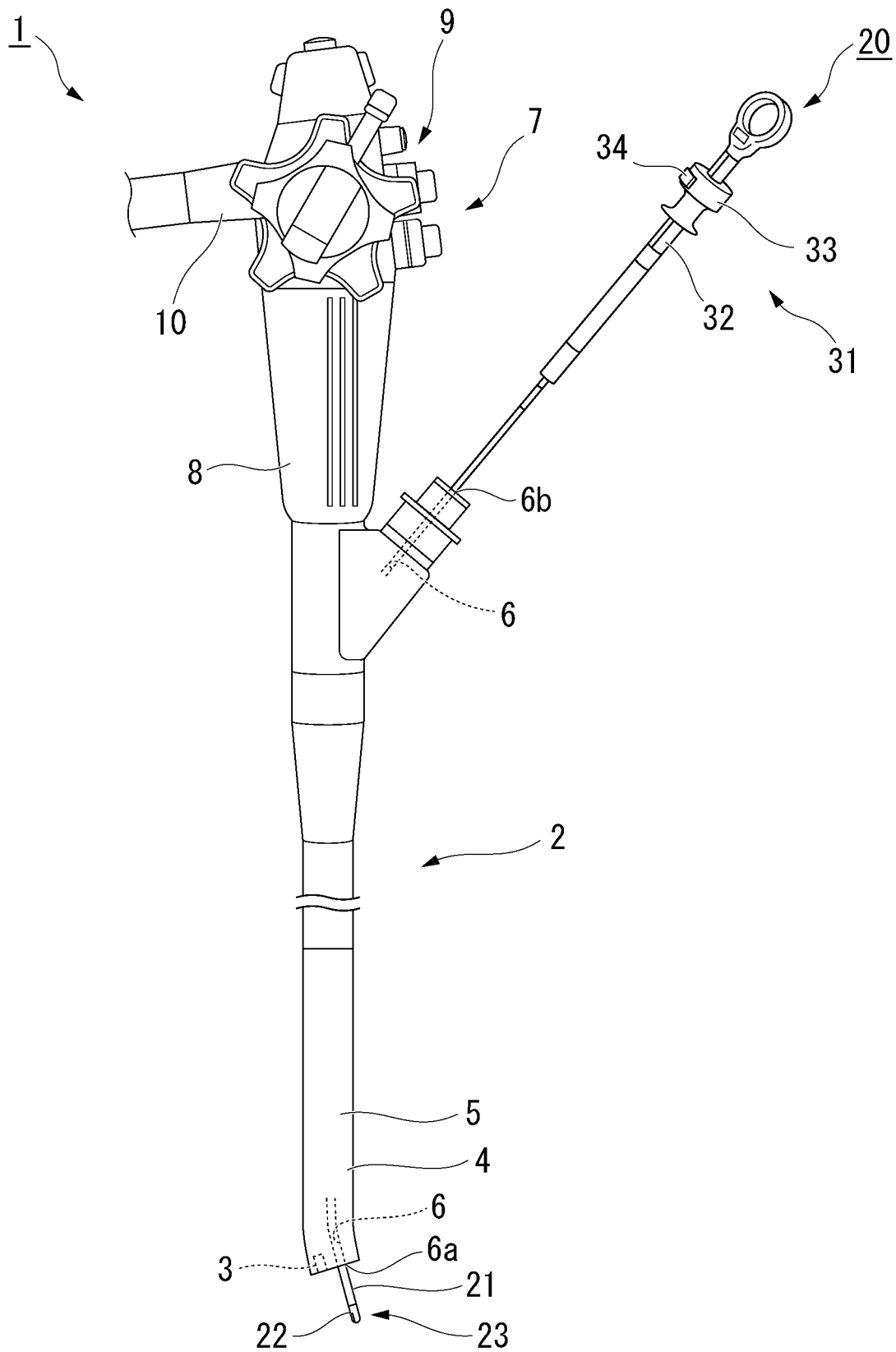
FIG. 1 is a view showing a state when a needle holder according to an exemplary embodiment is inserted into a flexible endoscope.

FIG. 1 is a view showing a state when a needle holder 20 according to the present embodiment is inserted into a flexible endoscope 1. The flexible endoscope 1 has an insertion portion 2 and an operation portion 7.

The insertion portion 2 has an imaging portion 3, an active bending portion 4, and a flexible portion 5. The imaging portion 3, the active bending portion 4, and the flexible portion 5 are disposed in this sequence from a distal end of the insertion portion 2. In an internal of the insertion portion 2, a channel 6 configured for inserting the needle holder 20 according to the present embodiment is formed therein. As the distal end of the insertion portion 2, a distal end opening portion 6a of the channel 6 is formed.

The imaging portion 3 is configured to be able to capture an image of a portion as a treatment object. The imaging portion 3 can capture the image of a grasping portion (grasper) 23 of the needle holder 20 which will be described below in a state when the needle holder 20 protrudes from the distal end opening portion 6a of the channel 6. The active bending portion 4 can actively bend according to an operation from the operation portion 7 by an operator. The flexible portion 5 is a tubular portion having flexibility.

The operation portion 7 is connected with the flexible portion 5. The operation portion 7 has a grip 8, an input portion 9, a distal end opening portion 6b of the channel 6, and a universal cord 10. The grip 8 is a portion for the operator to grasp. The input portion 9 is configured to receive an operation input for the bending operation of the active bending portion 4. The universal cord 10 is configured to output the image captured by the imaging portion 3 to the outside. The universal cord 10 can connect to a display apparatus such as a LCD display and the like via an image processing device such as a processor and the like.

Figure 2:
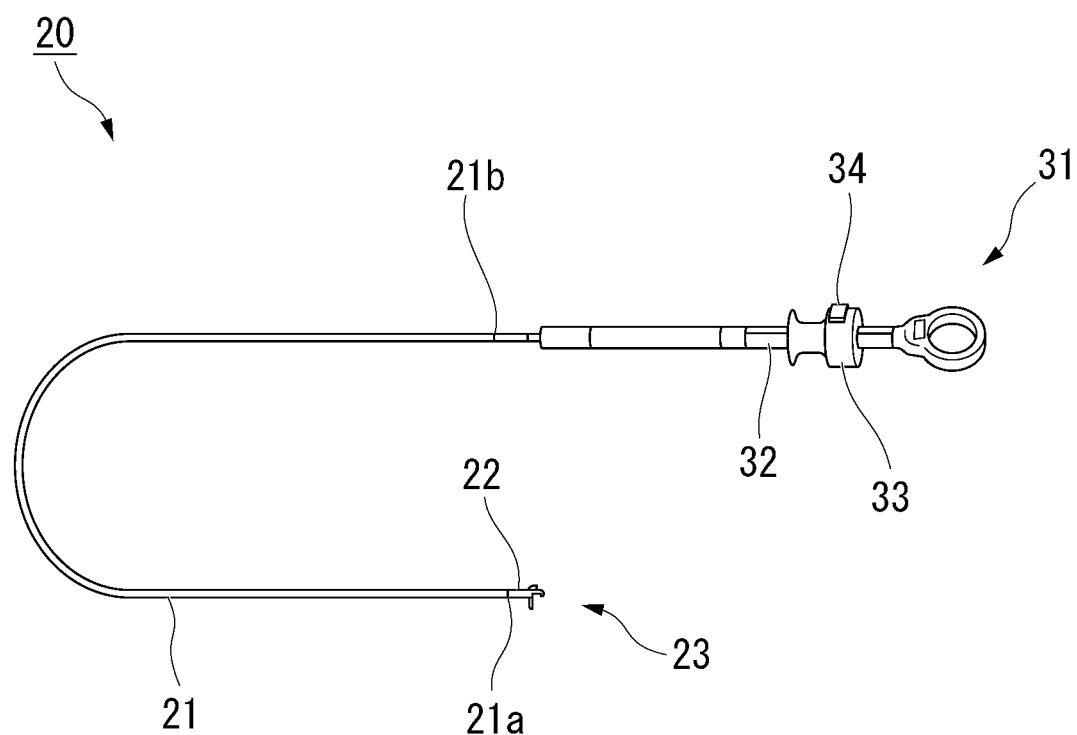
FIG. 2 is an overall view of the needle holder.

FIG. 2 is an overall view of the needle holder 20. The needle holder 20 has a flexible tube portion 21, a rigid portion 22, a grasping portion 23, and an operation portion 31. The flexible tube portion 21 is an elongated member extending from a distal end 21a to a proximal end 21b having flexibility. As shown in FIG. 1, the flexible tube portion 21 is insertable into the channel 6 of the flexible endoscope 1. In the state in which the flexible tube portion 21 is inserted into the channel 6, the distal end 21a of the flexible tube portion 21 can be protruded from and retracted into the distal end opening portion 6a of the channel 6. The distal end 21a of the flexible tube portion 21 can enter the imaging view field of the imaging portion 3 of the flexible endoscope 1 and be imaged by the imaging portion 3.

The rigid portion 22 is disposed at the distal end 21a of the flexible tube portion 21. The rigid portion 22 is formed from a rigid material. The grasping portion 23 is disposed at the rigid portion 22. The operation portion 31 is disposed at the proximal end 21b of the flexible tube portion 21.

Figure 3:
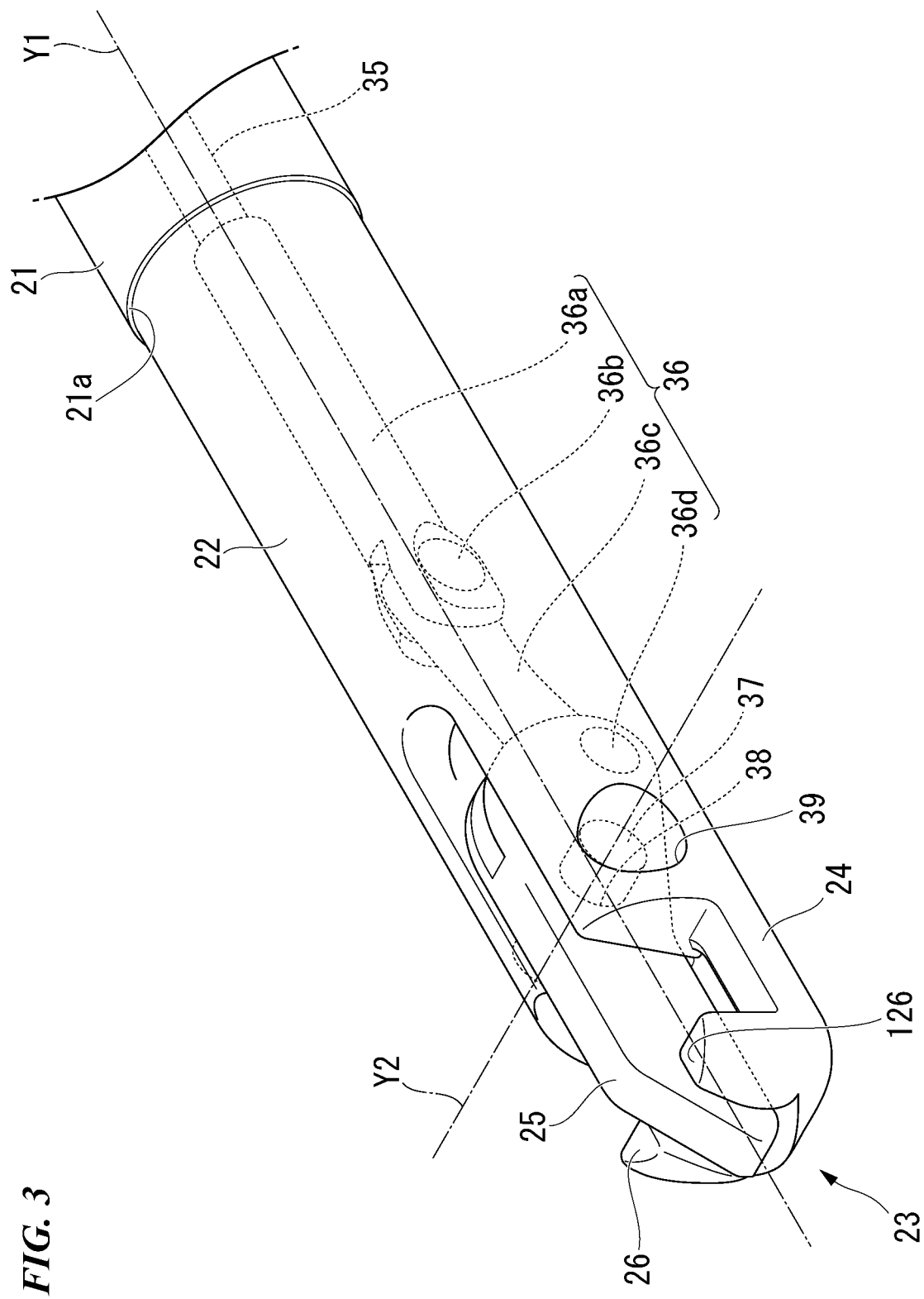
FIG. 3 is a perspective view showing a grasping portion of the needle holder and a state when a first grasping member and a second grasping member are closed.
Figure 4:
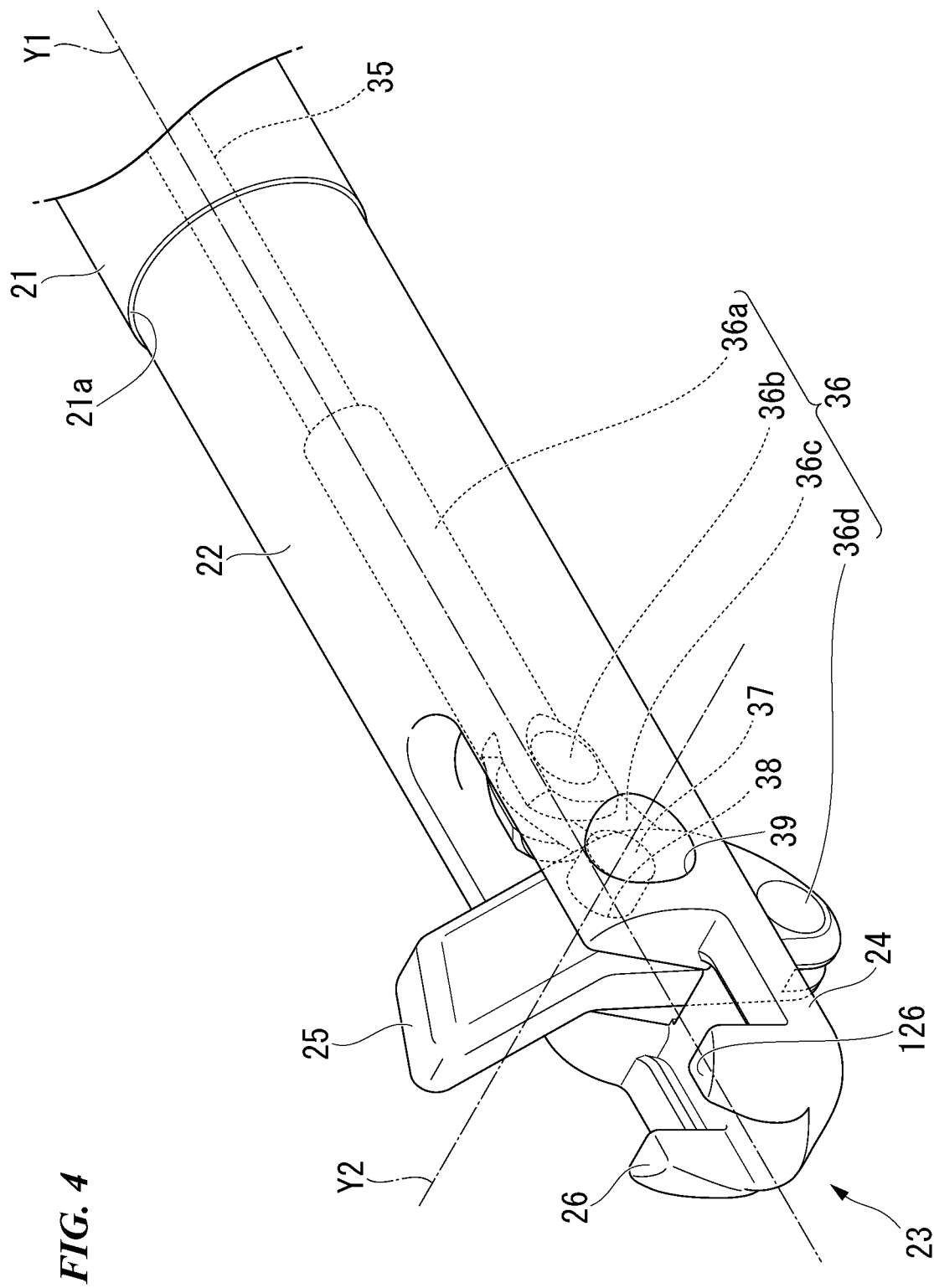
FIG. 4 is a perspective view showing the grasping portion of the needle holder and a state when a first grasping member and a second grasping member are opened.

FIG. 3 and FIG. 4 are perspective views showing the grasping portion 23 of the needle holder 20. The grasping portion 23 has a first grasping member (first jaw) 24, a second grasping member (second jaw) 25, a first protrusion portion (protrusion portion) 26, and a second protrusion portion 126. The first grasping member 24 and the second grasping member 25 are configured to be operable to be opened and closed. FIG. 3 shows the state when the first grasping member 24 and the second grasping member 25 are closed, and FIG. 4 shows the state when the first grasping member 24 and the second grasping member 25 are opened.

The first grasping member 24 is disposed to extend from the distal end of the rigid portion 22. The first grasping member 24 extends along a longitudinal axis Y1 of the flexible tube portion 21. In the needle holder 20 according to the present embodiment, the first grasping member 24 and the rigid portion 22 are integrally molded.

The second grasping member 25 is connected to the rigid portion 22 so as to be opened and closed with respect to the first grasping member 24. More specifically, for example, by inserting a connection shaft member 37 into a penetration hole 38 formed on the second grasping member 25 and a penetration hole 39 on the rigid portion 22, the second grasping member 25 is rotatably connected to the rigid portion 22. The second grasping member 25 is rotatable around a longitudinal axis Y2 of the connection shaft member 37.

The first protrusion portion 26 and the second protrusion portion 126 are disposed at the distal end portion of the first grasping member 24, and protrude in a direction intersecting to the longitudinal axis Y1. The first protrusion portion 26 and the second protrusion portion 126 are formed as a pair to sandwich the longitudinal axis Y1 of the flexible tube portion 21, and in the state when the first grasping member 24 and the second grasping member 25 are closed, the distal end portion of the second grasping member 25 is positioned between the first protrusion portion 26 and the second protrusion portion 126.

As shown in FIG. 1 and FIG. 2, the operation portion 31 has an operation portion main body 32, a slider 33, a fixing mechanism (not shown) configured to restrict an movement of the slider 33 with respect to the operation portion main body 32, and a release button 34 configured to release the fixation due to the fixing mechanism.

The distal end of the operation portion main body 32 is connected to the proximal end 21b of the flexible tube portion 21. The slider 33 is connected to the operation portion main body 32 so as to be advanceable and retractable with respect to the operation portion main body 32, and the slider 33 is advanceable and retractable along a direction of the longitudinal axis of the operation portion main body 32.

As shown in FIG. 3 and FIG. 4, an operation wire 35 extending along the longitudinal axis Y1 of the flexible tube portion 21 is disposed inside the flexible tube portion 21. The operation wire 35 is a flexible wire which is configured to transmit the operation force from the operation portion 31. The proximal end of the operation wire 35 is connected to the slider 33 of the operation portion 31. The distal end of the operation wire 35 is connected to a link mechanism 36. The link mechanism 36 is configured to have a first link member 36a, a first joint member 36b, a second link member 36c, and a second joint member 36d. The distal end of the operation wire 35 is connected to the first link member 36a. The first link member 36a is connected to the second link member 36c by the first joint member 36b. The second link member 36c is connected to the second grasping member 25 by the second joint member 36d. In other words, the distal end of the operation wire 35 and the second grasping member 25 are connected with each other via the link mechanism 36. Accordingly, the operation force for operating the second grasping member 25 to be opened and closed with respect to the first grasping member 24 is transmitted from the operation portion 31 to the second grasping member 25 via the operation wire 35 and the link mechanism 36.

The operation wire 35 can be advanced and retracted along the longitudinal axis Y1 of the flexible tube portion 21 by advancing and retracting the slider 33 along the operation portion main body 32. According to the present embodiment, the operation wire 35 can be pulled toward the side of the operation portion 31 by moving the slider 33 toward the proximal end side along the operation portion main body 32. The slider 33 is fixed at a desired position by the fixing mechanism. Accordingly, when the slider 33 is fixed in the state when the slider 33 is pulling the operation wire 35, it is possible to maintain the state in which the operation wire 35 is pulled. By pulling the operation wire 35 toward the side of the operation portion 31, the second grasping member 25 is moved toward the direction so as to be closed with respect to the first grasping member 24. Also, by pushing the operation wire 35 toward the side of the grasping portion 23, the second grasping member 25 is moved toward the direction so as to be opened with respect to the first grasping member 24.

Figure 5:
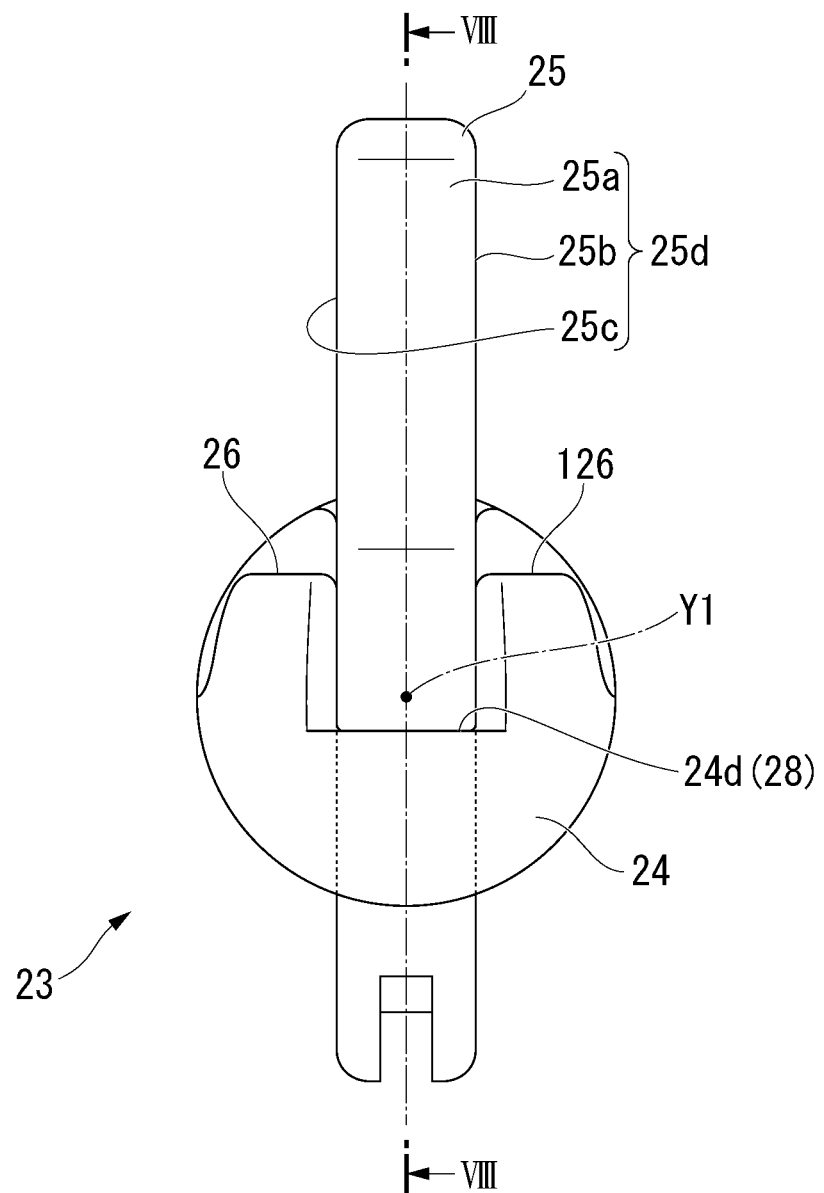
FIG. 5 is a view showing the grasping portion of the needle holder viewed from a direction of a longitudinal axis of a flexible tube portion.
Figure 6:
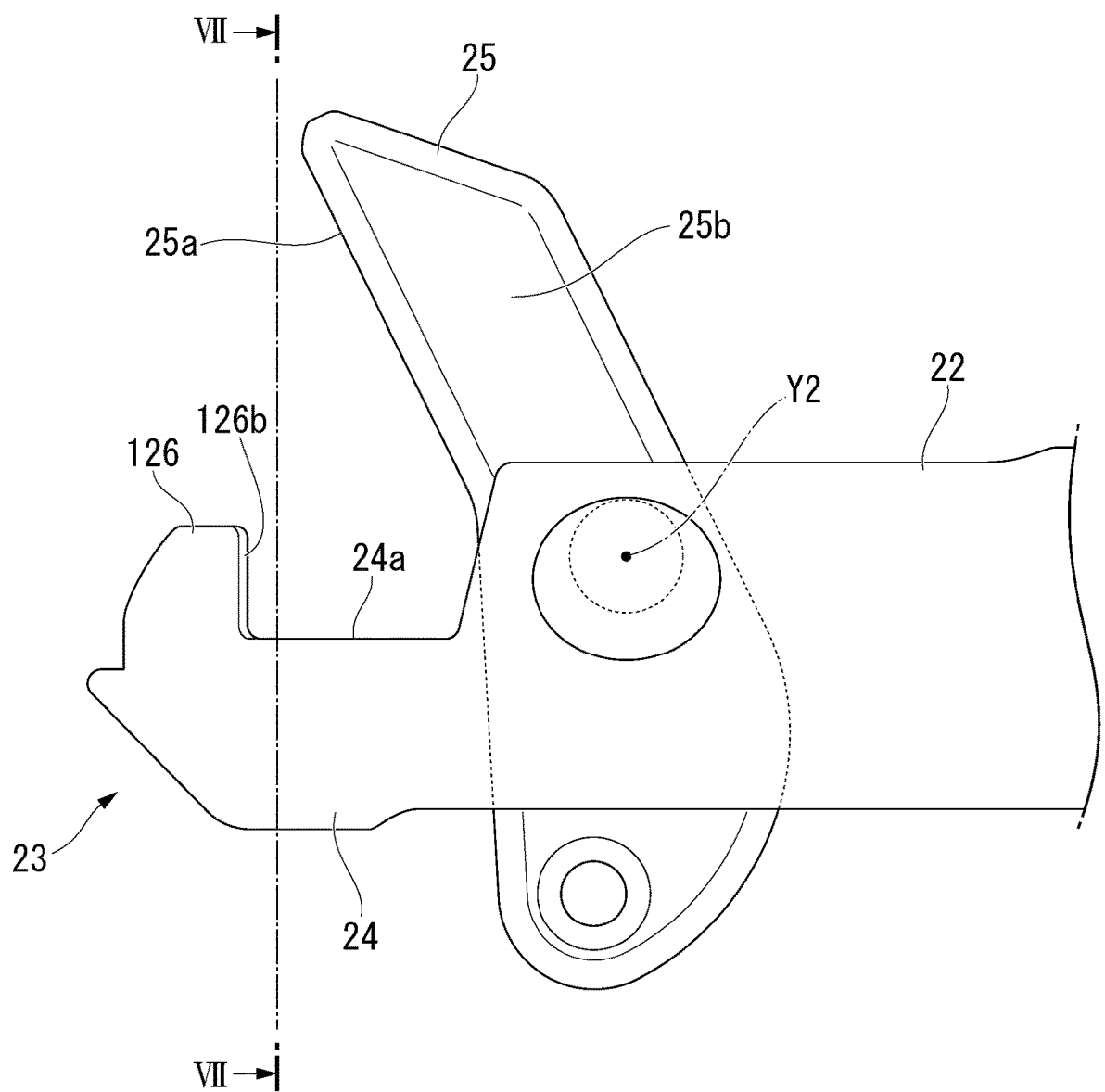
FIG. 6 is a view showing the grasping portion of the needle holder viewed from a direction of a longitudinal axis of a connection shaft member.
Figure 7:
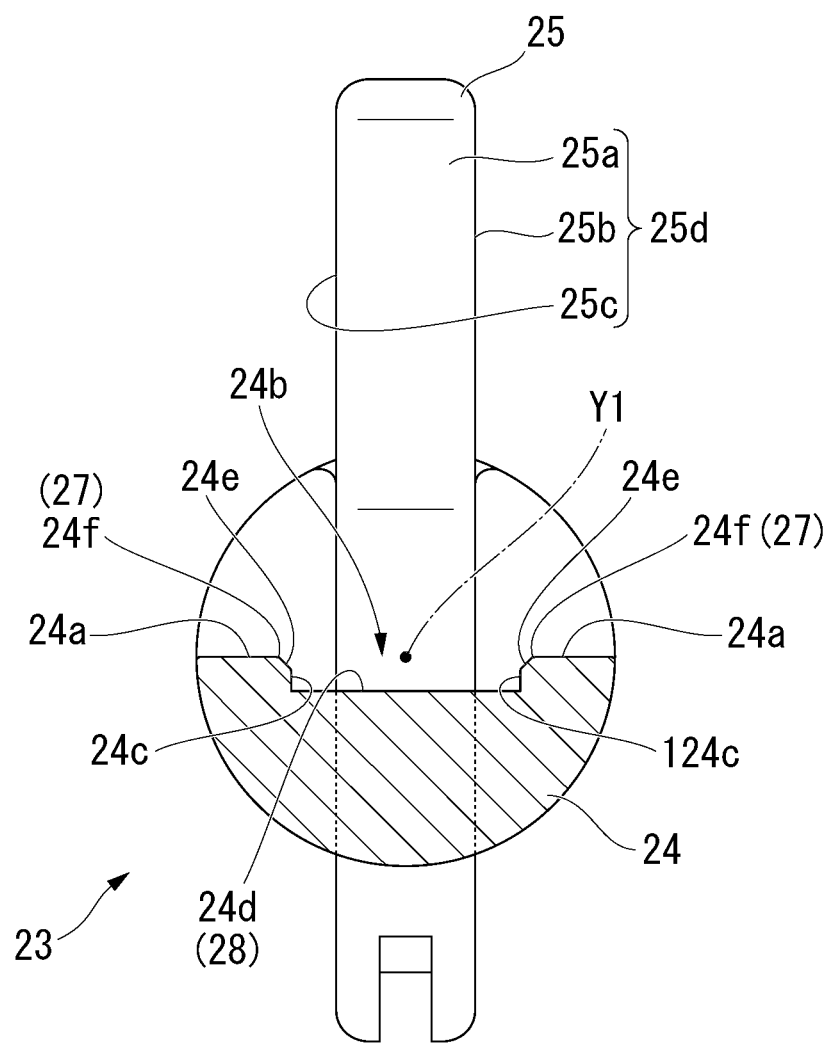
FIG. 7 is a cross-sectional view showing the grasping portion of the needle holder along line VII-VII in FIG. 6.
Figure 8:
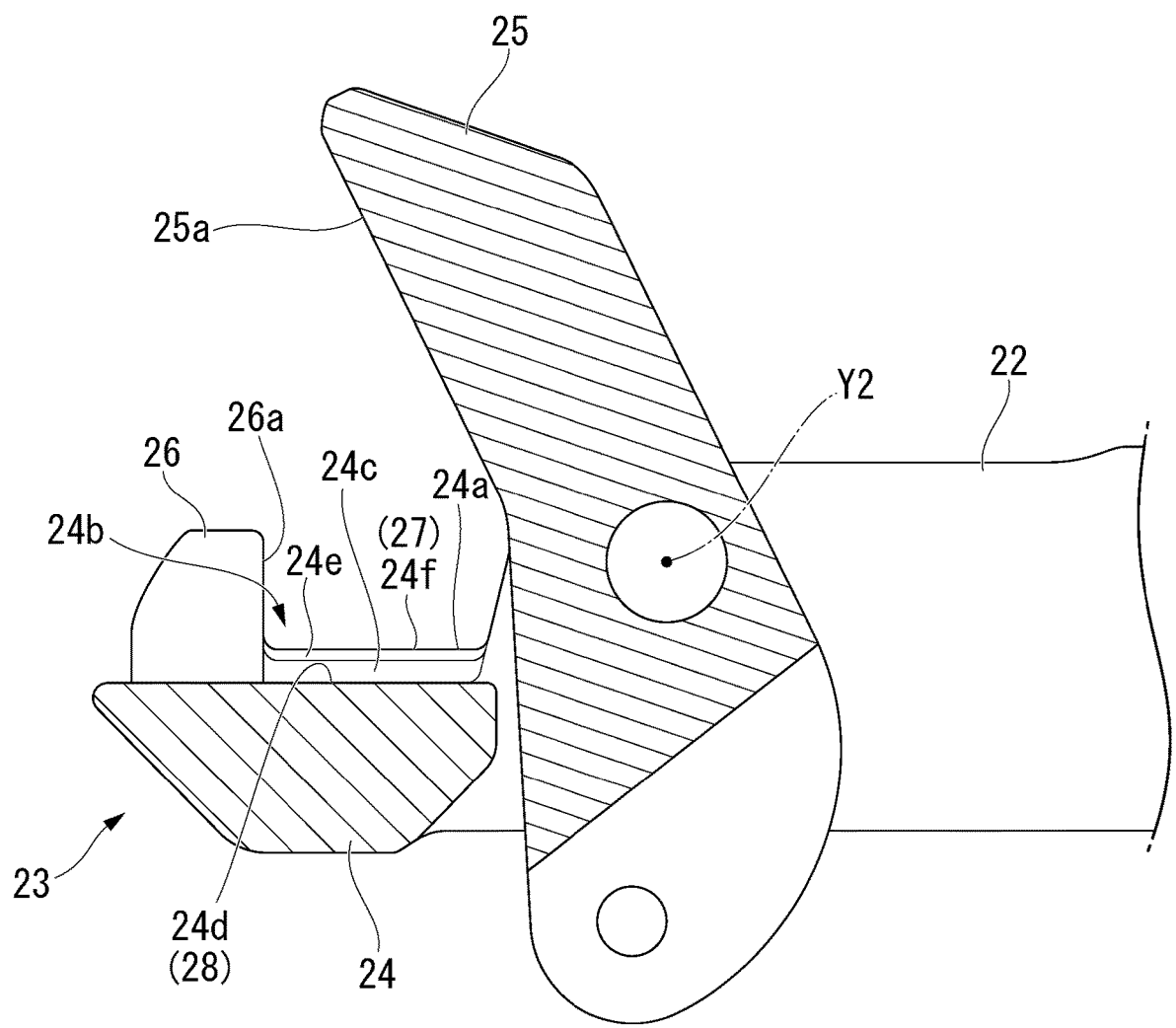
FIG. 8 is a cross-sectional view showing the grasping portion of the needle holder along line VIII-VIII in FIG. 5.

FIG. 5 is a view (front view) showing the grasping portion 23 of the needle holder 20 when viewed from a direction in which the longitudinal axis Y1 of the flexible tube portion 21 extends. FIG. 6 is a view (lateral view) showing the grasping portion 23 of the needle holder 20 when viewed from a direction in which the longitudinal axis Y2 of the connection shaft member 37 extends. FIG. 5 and FIG. 6 show the state in which the first grasping member 24 and the second grasping member 25 are opened. FIG. 7 is a cross-sectional view along the line VII-VII in FIG. 6. FIG. 8 is a cross-sectional view along the line VIII-VIII in FIG. 5. From FIG. 5 to FIG. 8, in order to make figures easy to view, the link mechanism 36 and the connection shaft member 37 are omitted.

As shown from FIG. 5 to FIG. 8, the first grasping member 24 has an outer edge surface 24a and a groove portion 24b.

The outer edge surface 24a is parallel to a plane defined by the direction in which the longitudinal axis Y1 of the flexible tube portion 21 extends and the direction in which the longitudinal axis Y2 of the connection shaft member 37 extends (hereinafter described as "reference plane"), and the outer edge surface 24a extends along the longitudinal axis Y1 of the flexible tube portion 21.

However, the configuration of the outer edge surface 24a according to the present embodiment is not limited to the above-described configuration. For example, the outer edge surface may be inclined with respect to the reference plane, and the outer edge surface may be a plane approaching the side of the second grasping member toward the distal end side.

The groove portion 24b is formed to extend along the longitudinal axis Y1 of the flexible tube portion 21. The groove portion 24b has a pair of surfaces extending in the direction intersecting the outer edge surface 24a, including a first internal wall surface (lateral surface) 24c and a second internal wall surface 124c, and a bottom surface 24d positioned between the first internal wall surface 24c and the second internal wall surface 124c. According to the present embodiment, each of the first internal wall surface 24c and the second internal wall surface 124c is intersected to the outer edge surface 24a and extends along the longitudinal axis Y1 of the flexible tube portion 21. The first internal wall surface 24c and the second internal wall surface 124c are formed as a pair of surfaces to sandwich the longitudinal axis Y1 of the flexible tube portion 21, and the second grasping member 25 is positioned between the first internal wall surface 24c and the second internal wall surface 124c in the state when the first grasping member 24 and the second grasping member 25 are closed. The bottom surface 24d is formed between the first internal wall surface 24c and the second internal wall surface 124c facing the first internal wall surface 24c. The bottom surface 24d is parallel to the outer edge surface 24a and extends along the longitudinal axis Y1 of the flexible tube portion 21. The groove portion 24b partitioned by the first internal wall surface 24c, the second internal wall surface 124c, and the bottom surface 24d is formed to extend along the longitudinal axis Y1 of the flexible tube portion 21, and the outer edge surfaces 24a are formed as a pair of surfaces to sandwich the groove portion 24b therebetween. The outer edge surface 24a is formed to intersect the first internal wall surface 24c and the second internal wall surface 124c of the groove portion 24b and positioned at the outer edge of the groove portion 24b.

A track guiding surface 24e and an edge 24f are formed at a boundary between the outer edge surface 24a and the first internal wall surface 24c and a boundary between the outer edge surface 24*a* and the second internal surface 124*c*. A boundary of the track guiding surface 24*e* and the outer edge surface 24*a* forms the edge 24*f* of the groove portion 24*b*. The outer edge surface 24*a* continuing to the edge 24*f* of the groove portion 24*b* extends to intersect with the first internal wall surface 24*c* (second internal wall surface 124*c*). Also, the outer edge surface 24*a* continuing to the edge 24*f* of the groove portion 24*b* extends to intersect with the track guiding surface 24*e*.

As shown in FIG. 7, the groove portion 24*b* of the first grasping member 24 has the first internal wall surface 24*c* (second internal wall surface 124*c*) intersecting with the bottom surface 24*d* and extending between the bottom surface 24*d* and the edge 24*f*, and the groove portion 24*b* of the first grasping member 24 has the track guiding surface 24*e* between the first internal wall surface 24*c* (second internal wall surface 124*c*) and the edge 24*f*. The track guiding surface 24*e* will be described in detail later.

The first protrusion portion 26 and the second protrusion portion 126 protrude from the distal end of the outer edge surface 24*a* and extend in the direction intersecting with the outer edge surface 24*a*. In other words, the first protrusion portion 26 and the second protrusion portion 126 protrude from the distal end of the outer edge surface 24*a* in the direction intersecting with the outer edge surface 24*a*.

Figure 13:
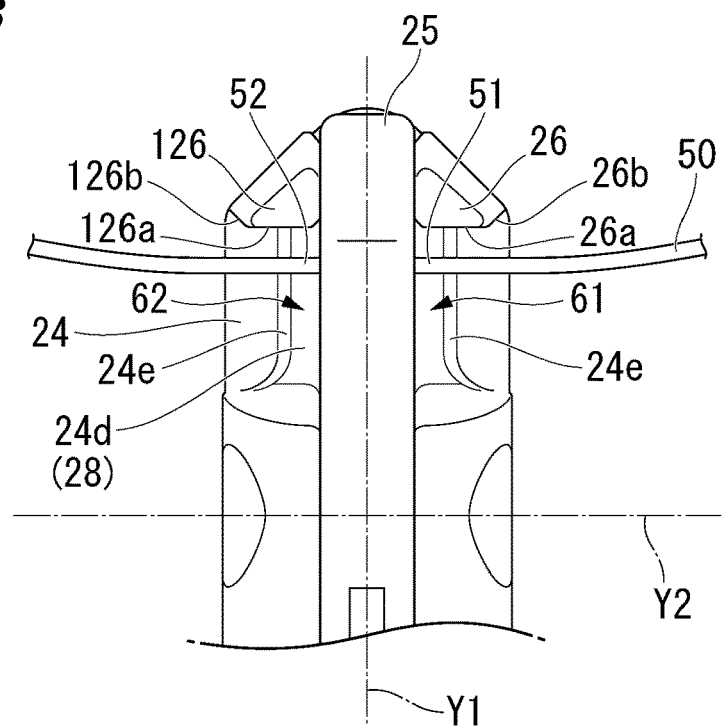
FIG. 13 is a view showing a state when the suture thread is held by the needle holder when viewed in a direction along an axis orthogonal to a longitudinal axis of the flexible tube portion and a longitudinal axis of the connection shaft member.

A receiving surface 26*a* and a hook surface 26*b* are formed on part of the outer circumferential surface of the first protrusion 26 (see FIG. 8 and FIG. 13).

The receiving surface 26*a* is formed at the proximal end side of the outer circumferential surface of the first protrusion 26. The hook surface 26*b* is formed as an inclined surface continuing to the receiving surface 26*a* and being inclined with respect to the receiving surface 26*a*, and the hook surface 26*b* is formed to at least have part of the outer circumferential surface of the first protrusion portion 26 that is the farthest from the longitudinal axis Y1 of the flexible tube portion 21. Also, a receiving surface 126*a* and a hook surface 126*b* are formed on part of the outer circumferential surface of the second protrusion portion 126 (see FIG. 6 and FIG. 13). The receiving surface 126*a* is formed at the proximal end side of the outer circumferential surface of the second protrusion 126. The hook surface 126*b* is formed as an inclined surface continuing to the receiving surface 126*a* and being inclined with respect to the receiving surface 126*a*, and the hook surface 126*b* is formed to at least have part of the outer circumferential surface of the second protrusion portion 126 that is the farthest from the longitudinal axis Y1 of the flexible tube portion 21. The receiving surface 26*a*, the hook surface 26*b*, the receiving surface 126*a*, and the hook surface 126*b* will be described in detail later.

As shown in FIG. 5 and FIG. 8, the second grasping member 25 has an outer circumferential surface 25*d* having a grasping surface 25*a*, a first lateral surface 25*b*, and a second lateral surface 25*c*. The first lateral surface 25*b* and the second lateral surface 25*c* are intersecting with the grasping surface 25*a*.

The grasping surface 25*a* is a surface facing the bottom surface 24*d* of the groove portion 24*b* of the first grasping member 24 when the second grasping member 25 is closed with respect to the first grasping member 24. According to the present embodiment, in the state when the grasping surface 25*a* of the second grasping surface 25 is positioned nearer to the bottom surface 24*d* side than the outer edge surface 24*a*, the grasping surface 25*a* of the second grasping member 25 is parallel to the bottom surface 24 and extends along the longitudinal axis Y1 of the flexible tube portion 21.

The first lateral surface 25*b* and the second lateral surface 25*c* are formed to a pair of surfaces sandwiching the longitudinal axis Y1 of the flexible tube portion 21, and the grasping surface 25*a* is positioned between the first lateral surface 25*b* and the second lateral surface 25*c*. The outer circumferential surface 25*d* of the second grasping member 25 is configured to at least have the first lateral surface 25*b*, the grasping surface 25*a*, and the second lateral surface 25*c*.

Next, the configuration of the needle holder 20 according to the present embodiment will be described in detail by referring to FIG. 9 to FIG. 14.

Figure 9:
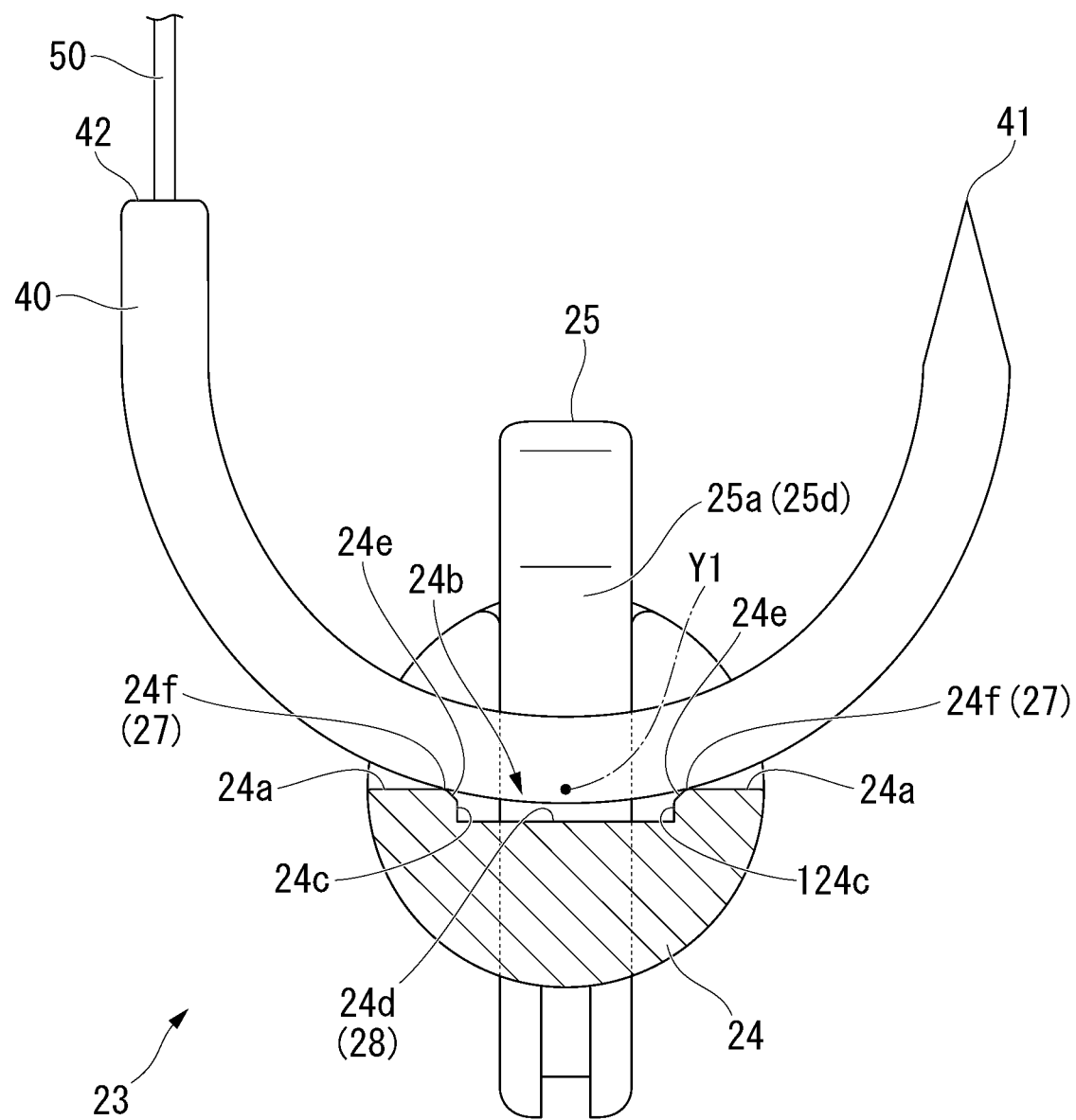
FIG. 9 is a cross-sectional view showing the grasping portion of the needle holder along line VII-VII in FIG. 6 and showing a state when a curved needle is held by the needle holder.
Figure 10:
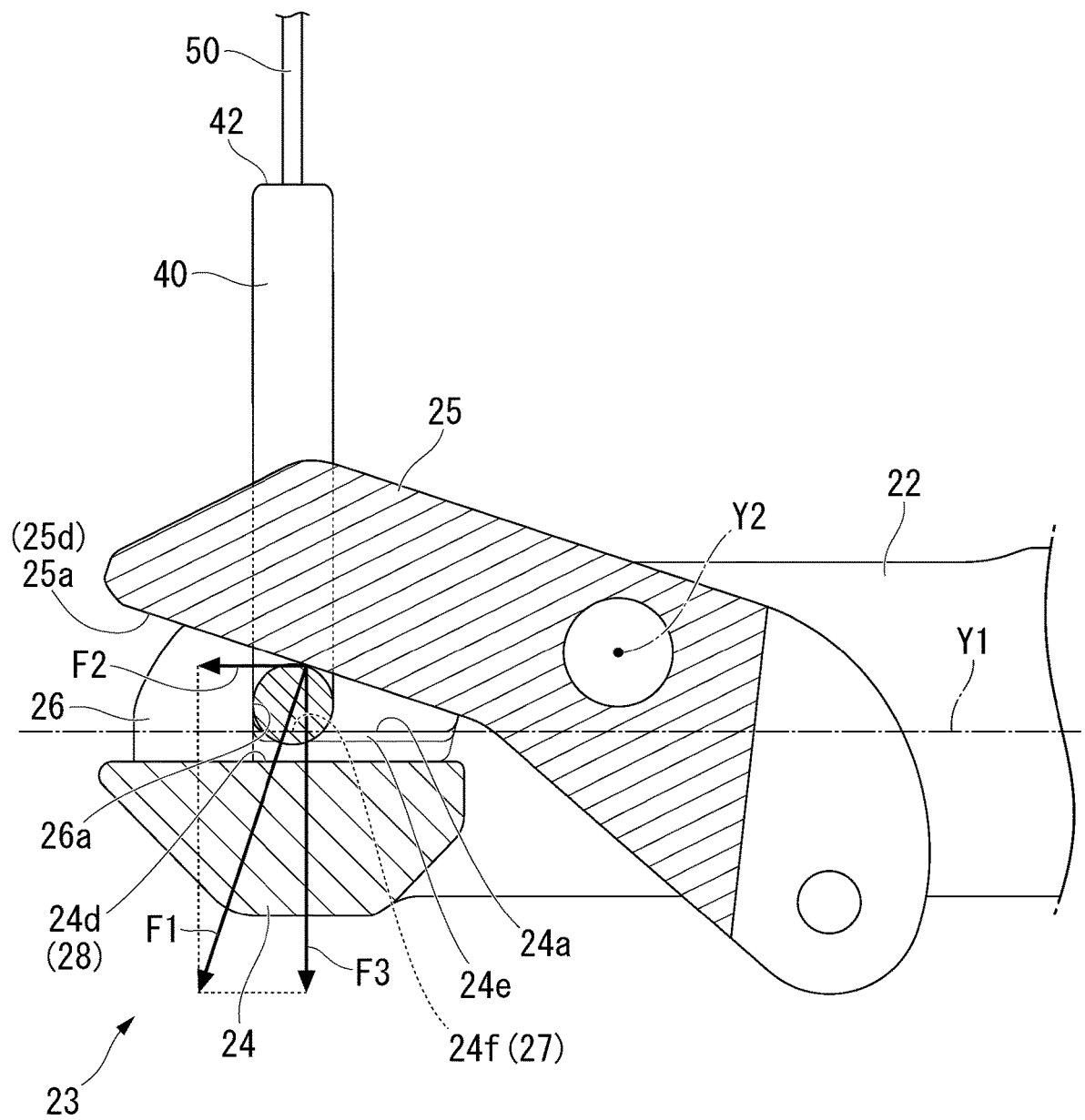
FIG. 10 is a cross-sectional view showing the grasping portion of the needle holder along line VIII-VIII in FIG. 5 and showing a state when a curved needle is held by the needle holder.
Figure 11:
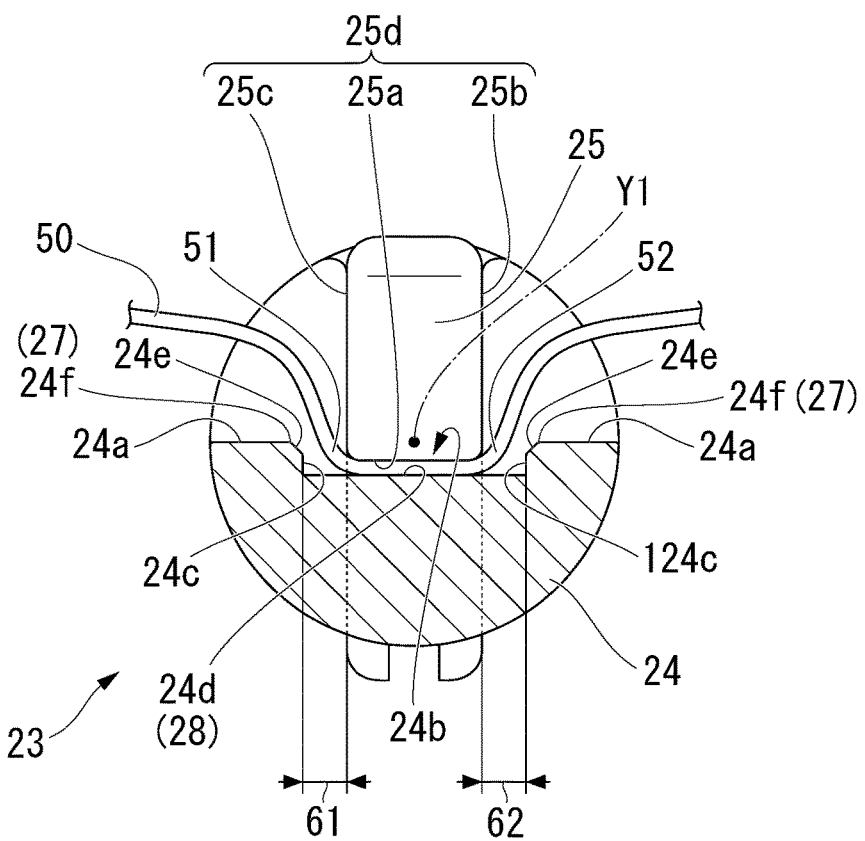
FIG. 11 is a cross-sectional view showing the grasping portion of the needle holder along line VII-VII in FIG. 6 and showing a state when a suture thread is held by the needle holder.
Figure 12:
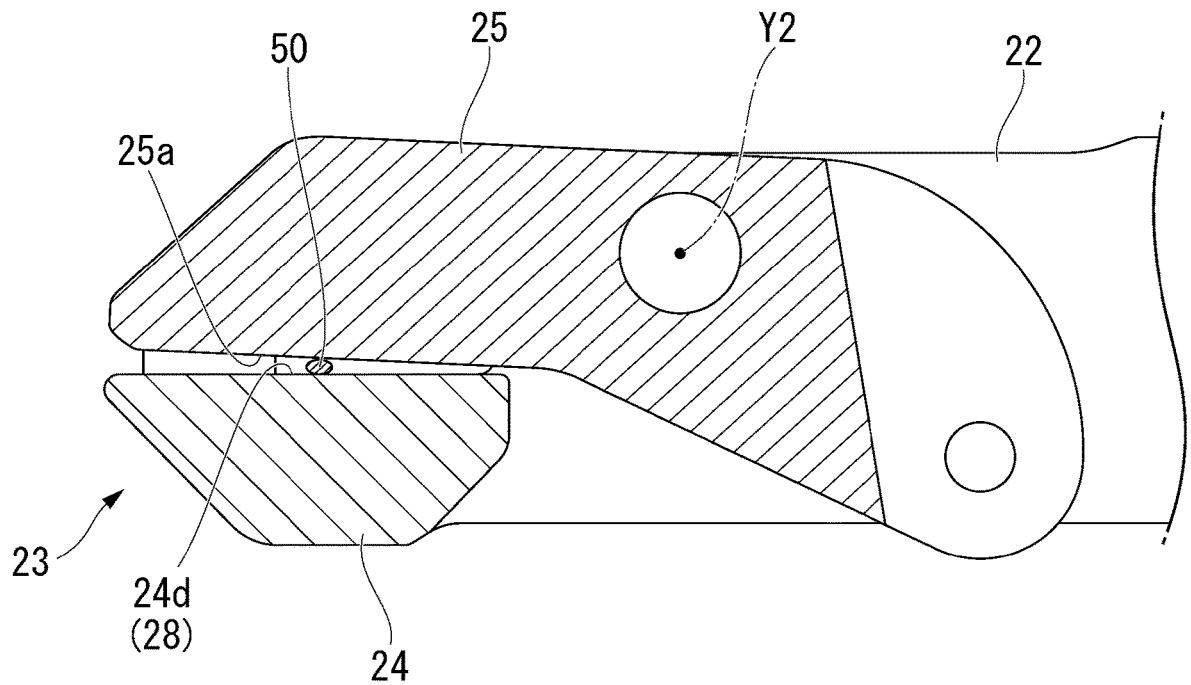
FIG. 12 is a cross-sectional view showing the grasping portion of the needle holder along line VIII-VIII in FIG. 5 and showing a state when a suture thread is held by the needle holder.

FIG. 9 is a cross-sectional view showing the grasping portion of the needle holder along line VII-VII in FIG. 6 and showing a state when the curved needle 40 is held by the needle holder 20. FIG. 10 is a cross-sectional view showing the grasping portion of the needle holder along line VIII-VIII in FIG. 5 and showing a state when the curved needle 40 is held by the needle holder 20. FIG. 11 is a cross-sectional view showing the grasping portion of the needle holder along line VII-VII in FIG. 6 and showing a state when the suture thread 50 is held by the needle holder 20. FIG. 12 is a cross-sectional view showing the grasping portion of the needle holder along line VIII-VIII in FIG. 5 and showing a state when the suture thread 50 is held by the needle holder 20. In FIG. 9 to FIG. 12, in order to make the figures easy to view, the link mechanism 36 and the connection shaft member 37 are omitted.

As shown in FIG. 9 and FIG. 10, the curved needle 40 has an arc shape with a predetermined curvature. The curved needle 40 has a needle tip 41 insertable into the tissue and a needle root 42 connected with the suture thread 50.

As shown in FIG. 1 to FIG. 4, the operation wire 35 is pulled to the operation portion 31 side such that a force to hold the curved needle 40 by the first grasping member 24 and the second grasping member 25 are generated and part of the curved needle 40 is held by the first grasping member 24 and the second grasping member 25.

As shown in FIG. 9 and FIG. 10, the needle holder 20 according to the present embodiment is configured to press and hold the curved needle 40 by the first grasping member 24, the second grasping member 25, and the first protrusion portion 26 (and the second protrusion portion 126. FIG. 10 is a cross-sectional view showing the grasping portion of the needle holder along line VIII-VIII in FIG. 5 such that only the first protrusion portion 26 can be viewed, however, similar to the first protrusion portion 26, the curved needle is also pressed and held by the second protrusion portion 126. When the curved needle 40 is held, a vector force F1 as the holding force is applied to the curved needle 40 from the outer circumferential surface 25*d* including the grasping surface 25*a* of the second grasping member 25. In the state when the curved needle 40 is held, the second grasping member 25 is inclined to form a predetermined angle with respect to the longitudinal axis Y1 of the flexible tube portion 21. Accordingly, the vector force F1 from the second grasping member 25 toward the distal end side and the outer edge surface 24*a* side is applied with respect to the curved needle 40.

As shown in FIG. 10, the vector force F1 is resolved to a vector force F2 in the direction along the longitudinal axis Y1 of the flexible tube portion 21 and a vector force F3 in the direction orthogonal to the direction of the vector force F2. The curved needle 40 is pressed to the first protrusion portion 26 (and the second protrusion portion 126) by the vector force F2, and the curved needle 40 is pressed to the first grasping member 24 by the vector force F3. Not only the curved needle 40 is pressed to the first grasping member 24 by the vector force F3 but also the curved needle 40 is pressed to the first protrusion portion 26 (and the second protrusion portion 126) by the vector force F2, the grasping portion 23 of the needle holder 20 can stably hold the curved needle 40.

The first protrusion portion 26 (and the second protrusion portion 126) can receive the vector force F2. The first protrusion portion 26 is configured to receive the vector force F2 by the receiving surface 26a formed in the part at the proximal end side of the outer circumferential surface of the first protrusion portion 26. The receiving surface 26a of the first protrusion portion 26 is formed to intersect with the outer edge surface 24a of the first grasping member 24 so as to be able to prevent the curved needle 40 from wavering due to the vector force F2 when the needle holder 20 holds the curved needle 40. In order to stably receive the vector force F2, the receiving surface 26a of the first protrusion portion 26 is preferably to be orthogonal to the outer edge surface 24a. Similar to the first protrusion portion 26, the second protrusion portion 126 is configured to receive the vector force F2 by the receiving surface 126a formed in the part at the proximal end side of the outer circumferential surface of the second protrusion portion 126.

The first grasping member 24 can receive the vector force F3. The first grasping member 24 is configured to receive the vector force F3 by the edge 24f of the groove portion 24b. As shown in FIG. 9 and FIG. 10, the curved needle 40 has the predetermined curvature such that part of the curved needle 40 enters the groove portion 24b of the first grasping member 24 when the curved needle 40 is held. In the state when the part of the curved needle 40 enters the groove portion 24b, the curved needle 40 comes in contact with the edge 24f of the groove portion 24b and the vector force F3 is received by the edge 24f of the groove portion 24b. In other words, a curved-needle pressing portion 27 is formed at the edge 24f of the groove portion 24b that is positioned at a boundary of the outer edge surface 24a and the first internal wall surface 24c (second internal wall surface 124c), and the curved needle 40 is held by the curved-needle pressing portion 27 pressing the curved needle 40 (the curved-needle pressing portion 27 receives the vector force F3).

The needle holder 20 according to the present embodiment is configured to support the curved needle 40 by the first grasping member 24, the second grasping member 25, the first protrusion portion 26, and the second protrusion portion 126 so as to hold the curved needle 40. More specifically, the needle holder 20 is configured to support the curved needle 40 by the curved-needle pressing portion 27 formed at the edge 24f of the groove portion 24b of the first grasping member 24, the outer circumferential surface 25d having the grasping surface 25a of the second grasping member 25, the receiving surface 26a of the first protrusion portion 26, and the receiving surface 126a of the second protrusion portion 126 so as to hold the curved needle 40. Accordingly, the curved needle 40 is not only pressed to the curved-needle pressing portion 27 by the vector force F3, but also pressed to the receiving surface 26a and the receiving surface 126a by the vector force F2 such that the curved needle 40 is stably held by the grasping portion 23 of the needle holder 20. In other words, the needle holder 20 according to the present embodiment can stably hold the curved needle 40.

As shown in FIG. 11 and FIG. 12, the needle holder 20 according to the present embodiment presses the suture thread 50 by the bottom surface 24d of the groove portion 24b of the first grasping member 24 and the grasping surface 25a of the second grasping member 25 so as to hold the suture thread 50. A thread pressing portion 28 is provided in the bottom surface 24d of the groove portion 24b of the first grasping member 24. When the suture thread 50 is held, the held part of the suture thread 50 is pressed and held by the thread pressing portion 28 and the grasping surface 25a of the second grasping member 25.

The needle holder 20 according to the present embodiment is used, for example, in the procedures of suturing the tissues in the gastrointestinal tract. The suture thread 50 used in the suturing procedures of the tissues in the gastrointestinal tract is a member having a smaller diameter than that of the curved needle 40, for example, the suture thread 50 has a diameter from 0.150 millimeters to 0.199 millimeters, and a diameter of the curved needle 40 is from 0.27 millimeters to 0.349 millimeters.

As shown in FIG. 12, when the suture thread 50 is held, the suture thread 50 is pressed by the thread pressing portion 28 provided in the bottom surface 24d of the groove portion 24b and the grasping surface 25a of the second grasping member 25. The bottom surface 24d and the grasping surface 25a are formed to face each other when the first grasping member 24 and the second grasping member 25 are closed. Also, the suture thread 50 is a small-diameter member. Accordingly, in the state in which the held part of the suture thread 50 is pressed by the thread pressing portion 28 and the grasping surface 25a, the bottom surface 24d and the grasping surface 25 is substantially parallel to each other. Also, at this time, the grasping surface 25a slightly enters the groove portion 24b and the grasping surface 25a is positioned at the side of the bottom surface 24d rather than the outer edge surface 24a.

The bottom surface 24d and the grasping surface 25a are substantially parallel to each other the vector force (holding force) along the longitudinal axis Y1 of the flexible tube portion 21 among the vector force (holding force) applied from the grasping surface 25a to the suture thread 50 hardly works. Accordingly, the suture thread 50 is uniformly pressed and held by the thread pressing portion 28 and the grasping surface 25a. In other words, the needle holder 20 according to the present embodiment can definitely hold the suture thread 50 without causing the stress to concentrate at the specific part of the suture thread 50.

As shown in FIG. 11, a first gap 61 (gap) is formed between the first internal wall surface 24c of the groove portion 24b of the first grasping member 24 and the second lateral surface 25c as part of the outer circumferential surface 25d of the second grasping member 25. Similarly, a second gap 62 is formed between the second internal wall surface 124c of the groove portion 24b of the first grasping member 24 and the first lateral surface 25b as part of the outer circumferential surface 25d of the second grasping member 25. Each of the first gap 61 and the second gap 62 is larger than the diameter of the suture thread 50.

When the needle holder 20 according to the present embodiment holds the suture thread 50, the needle holder 20 is configured to press the held part of the suture thread 50 by the thread pressing portion 28 and the grasping surface 25a, holds a first part (part) 51 continuing to an end of the held part of the suture thread 50 in the first gap 61 so as to be freely movable, and holds a second part 52 continuing to the other end of the held part of the suture thread 50 in the second gap 62 so as to be freely movable.

As shown in FIG. 11, the first part 51 of the suture thread 50 is not pressed by the first grasping member 24 and the second grasping member 25 such that the first part 51 is freely movable in the first gap. At the same time, the first part 51 of the suture thread 50 continues to one end of the held part of the suture thread 50 so as to be held by the grasping portion 23 of the needle holder 20. Similarly, the second part 52 of the suture thread 50 is not pressed by the first grasping member 24 and the second grasping member 25 such that the second part 52 is freely movable in the second gap 62. At the same time, the second part 52 of the suture thread 50 continues to the other end of the held part of the suture thread 50 so as to be held by the grasping portion 23 of the needle holder 20.

In the needle holder 20 according to the present embodiment, the first gap 61 and the second gap 62 are formed such that the first part 51 and the second part 52 continuing to the held part of the suture thread 50 can be held and caused to be freely movable. Accordingly, the shear force due to the first grasping member 24 and the second grasping member 25 are not applied to the first part 51 and the second part 52 of the suture thread 50. In other words, the needle holder 20 according to the present embodiment is configured to suitably prevent the suture thread 50 from being cut due to the shear force.

Also, in the needle holder 20 according to the present embodiment, both of the first gap 61 and the second gap 62 are formed, however, for example, in the case in which only the first gap 61 is formed, the suture thread 50 can be held without receiving the shear force so as to be freely movable at least in the first gap 61.

As shown in FIG. 11, the track guiding surface 24e is provide between the outer edge surface 24a and the first internal wall surface 24c, and between the outer edge surface 24a and the second internal wall surface 124c. A pair of the track guiding surfaces 24e are provided to sandwich the longitudinal axis Y1 of the flexible tube portion 21, and the first internal wall surface 24c, the bottom surface 24d, and the second internal wall surface 124c are positioned between the pair of track guiding surfaces 24e. The track guiding surface 24e is an inclined surface from the end portion of the outer edge surface 24a toward the groove portion 24b, and the track guiding surface 24e is configured to be able to guide the longitudinal axis (track) of the suture thread 50 with respect to the groove portion 24b. By providing the track guiding surface 24e, when the suture thread 50 is held by the needle holder 20, it is easy for the longitudinal axis of the suture thread 50 to be along the direction across the groove portion 24b (the direction interesting to the longitudinal axis Y1 of the flexible tube portion 21). The longitudinal axis of the suture thread 50 is guided to be along the direction across the groove portion 24b by the track guiding surface 24e such that it is easy to hold the suture thread 50 using the grasping portion 23 of the needle holder 20.

Figure 14:
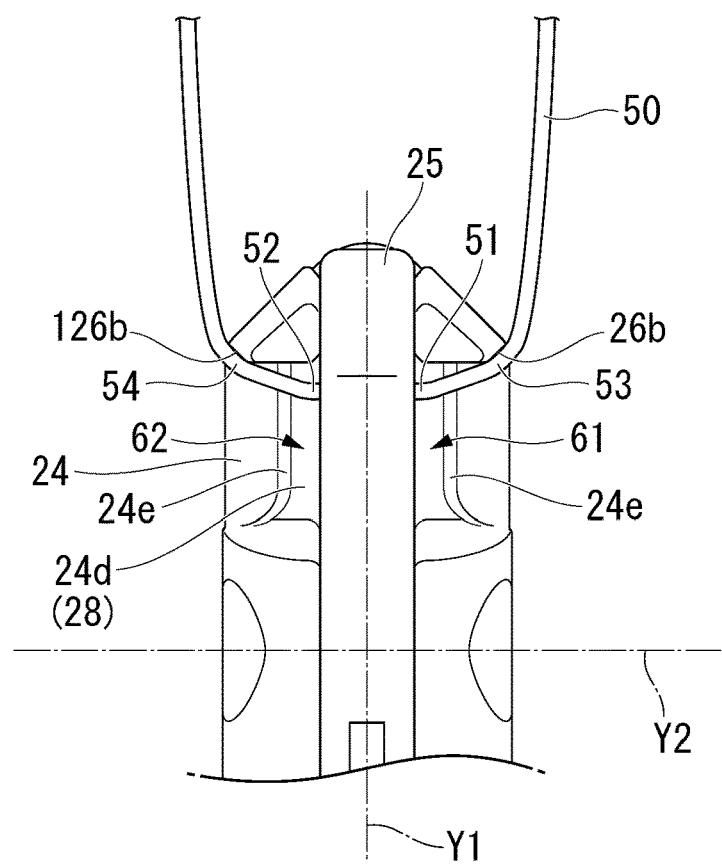
FIG. 14 is a view showing a state when the suture thread is pulled by the needle holder when viewed in the direction along the axis orthogonal to the longitudinal axis of the flexible tube portion and the longitudinal axis of the connection shaft member.

FIG. 13 is a view showing a state when the suture thread 50 is held by the needle holder 20 when viewed in a direction along the axis orthogonal to the longitudinal axis Y1 of the flexible tube portion 21 and the longitudinal axis Y2 of the connection shaft member 37. FIG. 14 is a view showing a state when the suture thread 50 is pulled by the needle holder 20 in the direction along the longitudinal axis Y1 of the flexible tube portion 21 and in a direction orthogonal to the longitudinal axis Y2 of the connection shaft member 37.

As shown in FIG. 13, the suture thread 50 is guided to be along the direction across the groove portion 24b and the suture thread 50 is held by the first grasping member 24 and the second grasping member 25.

A hook surface 26b is formed in part of the outer circumferential surface of the first protrusion portion 26. The hook surface 26b is formed to continue to the receiving surface 26a as an inclined surface with respect to the receiving surface 26a, and the hook surface 26b is formed to at least have part of the outer circumferential surface of the first protrusion portion 26 which is the farthest from the longitudinal axis Y1 of the flexible tube portion 21. The hook surface 26b is formed in the direction along the track of the suture thread 50 when the held suture thread 50 is pulled. Also, a hook surface 126b is formed in part of the outer circumferential surface of the second protrusion portion 126. The hook surface 126b is formed to continue to the receiving surface 126a as an inclined surface with respect to the receiving surface 126a, and the hook surface 126b is formed to at least have part of the outer circumferential surface of the second protrusion portion 126 which is the farthest from the longitudinal axis Y1 of the flexible tube portion 21. The hook surface 126b is formed in the direction along the track of the suture thread 50 when the held suture thread 50 is pulled.

As shown in FIG. 14, in the state when the held part of the suture thread 50 is pressed by the bottom surface 24d (thread pressing portion 28) and the grasping surface 25a, a third part 53 and a fourth part 54 of the suture thread 50 positioned outside the groove portion 24b are hooked by the hook surface 26b and the hook surface 126b respectively. When the suture thread 50 is pulled, in addition to the held part of the suture thread 50, the third part 53 and the fourth part 54 of the suture thread 50 also receive the tensile force. Accordingly, it is difficult for the suture thread to be damaged. Furthermore, the part holding the held part of the suture thread 50 between the bottom surface 24d (thread pressing portion 28), the hook surface 26b, and the hook surface 126b can apply the tensile force with respect to the suture thread 50 such that it is possible to pull the suture thread 50 with a large tensile force.

When the suture thread 50 is pulled by the needle holder 20, according to the direction in which the suture thread 50 is pulled, only the third part 53 of the suture thread 50 may be pulled by the hook surface 26b and only the fourth part 54 of the suture thread 50 may be pulled by the hook surface 126b.

As described above, the needle holder 20 according to the present embodiment is configured to press the curved needle 40 by the curved-needle pressing portion 27 disposed at the edge 24f of the groove portion 24b of the first grasping member 24, the outer circumferential surface 25d including the grasping surface 25a of the second grasping member 25, the receiving surface 26a of the first protrusion portion 26, and the receiving surface 126a of the second protrusion portion 126. Accordingly, the needle holder 20 can stably hold the curved needle 40.

The needle holder 20 according to the present embodiment is configured to uniformly press the held part of the suture thread 50 by the thread pressing portion formed in the bottom surface 24d of the groove portion 24b and the grasping surface 25a of the second grasping member 25. Accordingly, the needle holder 20 can hold the suture thread 50 without causing the stress to be concentrated at the specific part of the suture thread 50.

Furthermore, the needle holder 20 according to the present embodiment has the first gap 61 and the second gap 62 formed therein such that when the needle holder 20 holds the suture thread 50, the first part 51 and the second part 52 continuing to the held part of the suture thread 50 can be held to be freely movable, and the shear force by the first grasping member 24 and the second grasping member 25 are not applied to the first part 51 and the second part 52 respectively. Accordingly, the needle holder 20 is configured to suitably prevent the suture thread 50 from being cut by the shear force.

The needle holder 20 according to the present embodiment is configured to be able to stably hold the curved needle 40 and hold the suture thread 50 without any damage.

Figure 15:
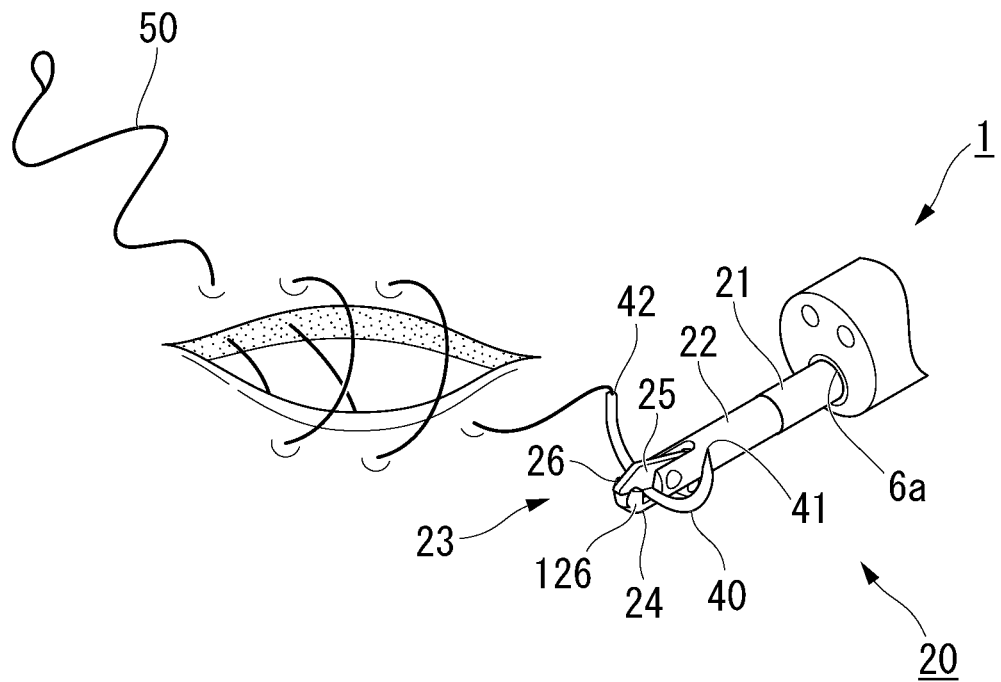
FIG. 15 is a view showing procedures of a method of using the needle holder.
Figure 16:
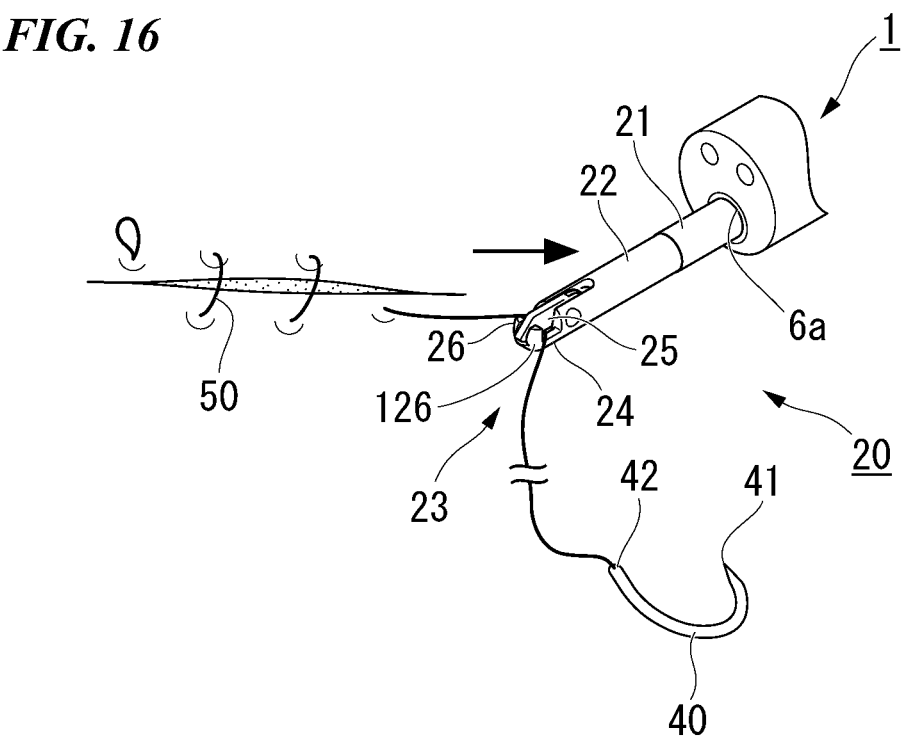
FIG. 16 is a view showing procedures of a method of using the needle holder.

Next, surgical procedures (usage method) of using the needle holder 20 according to the present embodiment will be described by referring to FIG. 15 and FIG. 16. FIG. 15 and FIG. 16 are views showing the procedures of the usage method of the needle holder 20.

The flexible endoscope 1 is inserted into the gastrointestinal tract from the natural opening of the patient.

Subsequently, as shown in FIG. 15, the first grasping member 24 and the second grasping member 25 of the needle holder 20 are protruded from the distal end opening portion 6a of the channel 6 of the flexible endoscope 1. In the state when the first grasping member 24 and the second grasping member 25 are protruded, the curved needle 40 having the needle root 42 and the needle tip 41 is held between the first grasping member 24 and the second grasping member 25.

In the step of holding the curved needle 40 by the needle holder 20, the curved needle 40 is held by the first grasping member 24, the second grasping member 25, the first protrusion portion 26, and the second protrusion portion 126 of the needle holder 20. At this time, as shown in FIG. 9 and FIG. 10, the curved needle 40 is pressed by the edge 24f (curved-needle pressing portion 27) of the groove portion 24b of the first grasping member 24, the outer circumferential surface 25d including the grasping surface 25a of the second grasping member 25, the first protrusion portion 26, and the second protrusion portion 126 such that the curved needle 40 is stably held.

Subsequently, as shown in FIG. 15, the curved needle 40 is held by the needle holder 20 and punctured into the target tissues in the gastrointestinal tract by multiple times, and the suture thread 50 is hooked on the target tissues. Thereafter, the curved needle 40 is released from the needle holder 20.

Subsequently, as shown in FIG. 16, while maintaining the first grasping member 24 and the second grasping member 25 to be protruded from the distal end opening portion 6a of the channel 6 of the flexible endoscope 1, the suture thread 50 connected to the needle root 42 of the curved needle 40 is held between the first grasping member 24 and the second grasping member 25.

In the step of holding the suture thread by the needle holder 20, the held part of the suture thread 50 is held by the first grasping member 24 and the second grasping member 25 of the needle holder 20. At this time, as shown in FIG. 11 and FIG. 12, the held part of the suture thread 50 is pressed and held by the bottom surface 24d (thread pressing portion 28) of the groove portion 24b of the first grasping member 24 and the grasping surface 25a of the second grasping member 25. In the state when the held part of the suture thread 50 is pressed by the bottom surface 24d of the groove portion 24b of the first grasping member 24 and the grasping surface 25a of the second grasping member 25, the bottom surface 24d and the grasping surface 25a are substantially parallel to each other. Accordingly, the needle holder 20 is configured to be able to hold the suture thread 50 without concentrating the stress at the specific part of the suture thread 50.

The needle holder 20 is configured to press the held part of the suture thread 50 by the bottom surface 24d and the grasping surface 25a, holds a first part 51 continuing to one end of the held part of the suture thread 50 in the first gap 61 so as to be freely movable, and holds a second part 52 continuing to the other end of the held part of the suture thread 50 in the second gap 62 so as to be freely movable. Accordingly, the needle holder 20 is configured to be able to hold the suture thread 50 without applying the shear force to the suture thread 50.

Subsequently, as shown in FIG. 16, in the state when the suture thread 50 is held by the needle holder 20, the suture thread 50 is pulled by pulling the held part of the suture thread 50 in the direction apart from the target tissues to apply the tension to the suture thread 50 so as to fasten the target tissues (circumferential suture).

In the step of pulling the suture thread 50 by the needle holder 20, as shown in FIG. 14, the third part 53 and the fourth part 54 of the suture thread 50 positioned outside the groove portion 24b are hooked by the hook surface 26b and the hook surface 126b respectively. The pulling force applied to the suture thread 50 is dispersed to the held part of the suture thread 50, the third part 53, and the fourth part 54 such that it is difficult to cause damage to the suture thread 50 and it is possible to pull the suture thread 50 with a large force according to the situation of the suturing procedures.

As described above, according to the method of using the needle holder according to the present embodiment, the curved needle 40 can be stably held by the needle holder 20, and further the suture thread 50 can be held without any damage. Accordingly, for example, it is possible to efficiently proceed with the procedures of suturing the target tissues in the gastrointestinal tract using the flexible endoscope 1.

The exemplary embodiments have been described above with reference to the drawings, but the technical scope of the present disclosure is not limited to the embodiments and may include various modifications without departing from the scope of the disclosure.

For example, in the above-described embodiment, the example of integrally molding the first grasping member 24 and the rigid portion 22 is described, however, the first grasping member and the rigid portion may be configured separately. In this case, the first grasping member may be rotatably connected to the rigid portion and operable to be opened and closed with respect to the second grasping member. In addition to the second grasping member, the first grasping member is configured to be rotatable such that the range of the open/close operation by the pair of grasping members can be enlarged.

For example, in the above-described embodiment, the example of the link mechanism 36 having the first link member 36a, the first joint member 36b, the second link member 36c, and the second joint member 36d is described, however, the configuration of the link mechanism is not limited thereto. The link mechanism only has to be configured to transmit the operation force transmitted from the operation wire 35 to the second grasping member 25, and the configuration thereof is not particularly limited. Also, the operation wire 35 and the second grasping member 25 may be directly connected with each other such that the link mechanism may not be configured. In this case, the configuration of the needle holder can be simplified.

What is claimed is:

1. A needle holder comprising:
   a flexible tube; and
   a grasper located distally relative to the flexible tube, the grasper comprising:
   a first jaw including a groove and a protrusion, the groove extending along a longitudinal axis, the protrusion being disposed at a distal end portion of the first jaw and protruding in a protruding direction intersecting the longitudinal axis; and a second jaw connected to the first jaw, the second jaw being operable to open and close with respect to the first jaw;

wherein the protrusion includes:

a proximal surface formed on a proximal end of the protrusion so as to face in a proximal direction along the longitudinal axis, and a hook surface extending continuously and outwardly from the proximal surface in a width direction and being inclined with respect to the proximal surface in a distal direction, the width direction being orthogonal to the protruding direction and the longitudinal axis.

2. The needle holder according to claim 1, wherein the grasper is configured to:

hold a curved needle between the second jaw and the first jaw, and hold a suture thread connected to the curved needle by pressing a first part of the suture thread between: (i) a bottom surface of the groove of the first jaw and (ii) the second jaw such that a second part of the suture thread, which is not pressed between the bottom surface and the second jaw, passes through a gap formed between: (i) a first wall surface of the groove and (ii) the second jaw.

3. The needle holder according to claim 2, wherein the hook surface is configured to hook a third part of the suture thread that extends outside the groove in the state when the first part of the suture thread is pressed between the bottom surface of the groove and the second jaw.

4. The needle holder according to claim 1, wherein the hook surface extends in the protruding direction.

5. The needle holder according to claim 1, wherein:

the groove includes a bottom surface facing the second jaw, and the second jaw includes a grasping surface facing the bottom surface.

6. The needle holder according to claim 5, wherein a length of the bottom surface in the width direction is longer than a length of the grasping surface in the width direction.

7. The needle holder according to claim 5, wherein:

the groove includes a first wall surface and a second wall surface, the first wall surface and the second wall surface extend from the bottom surface and extend in the protruding direction, and a length between the first wall surface and the second wall surface in the width direction is longer than a length of the grasping surface in the width direction.

8. The needle holder according to claim 7, wherein the first jaw includes an outer edge surface extending from a bottom of the proximal surface along the longitudinal axis.

9. The needle holder according to claim 8, wherein the outer edge surface is orthogonal to the first wall surface and the second wall surface.

10. The needle holder according to claim 8, wherein the first jaw includes a guiding surface located between the first wall surface and the outer edge surface.

11. A needle holder comprising:

a flexible tube; and a grasper located distally relative to the flexible tube, the grasper comprising:

a first jaw including:

a bottom surface;

a first wall surface extending from the bottom surface, the first wall surface extending in a height direction intersecting a longitudinal axis of the flexible tube;

a second wall surface extending from the bottom surface, the second wall surface extending in the height direction, wherein the bottom surface, the first wall surface and the second wall surface form a groove;

a first protrusion including a first proximal surface facing in a proximal direction along the longitudinal axis; and a second protrusion including a second proximal surface facing in the proximal direction, the first protrusion and the second protrusion being located in a distal end portion of the first jaw, and the first protrusion and the second protrusion protruding in the height direction; and a second jaw movable relative to the first jaw between an open position and a closed position, wherein the first jaw includes:

a first outer edge surface extending in the proximal direction from the first proximal surface of the first protrusion, the first outer edge surface being transverse to the height direction, and a first guiding surface extending continuously from an inner edge of the first outer edge surface to the first wall surface so as to be transverse to the first outer edge surface and the first wall surface.

12. The needle holder according to claim 11, wherein the first guiding surface is inclined so as to extend inwardly along a width direction and be inclined towards the bottom surface in the height direction, the width direction being orthogonal to the height direction and the longitudinal axis.

13. The needle holder according to claim 11, wherein:

the second jaw includes a first lateral surface and a second lateral surface, the first wall surface is spaced apart from the first lateral surface when the second jaw is in the closed position, and the second wall surface is spaced apart from the second lateral surface when the second jaw is in the closed position.

14. The needle holder according to claim 11, wherein a distal end portion of the second jaw is located between the first protrusion and the second protrusion when the second jaw is in the closed position.

15. The needle holder according to claim 11, wherein:

the first protrusion and the second protrusion respectively include a first hook surface and a second hook surface, the first hook surface extends continuously and outwardly from the first proximal surface in a width direction and is inclined with respect to the first proximal surface in a distal direction, the width direction being orthogonal to the height direction and the longitudinal axis, and the second hook surface extends continuously and outwardly from the second proximal surface in the width direction and is inclined with respect to the second proximal surface in the distal direction.

16. The needle holder according to claim 11, wherein a distal end of the first protrusion and a distal end of the second protrusion are formed separately.

17. The needle holder according to claim 11, wherein:

the second jaw includes a grasping surface facing the bottom surface, and a length of the bottom surface in a width direction is longer than a length of the grasping surface in the width direction, the width direction being orthogonal to the height direction and the longitudinal axis.

18. The needle holder according to claim 11, wherein:
    the second jaw includes a grasping surface facing the bottom surface, and
    a length between the first wall surface and the second wall surface in a width direction is longer than a length of the grasping surface in the width direction, the width direction being orthogonal to the height direction and the longitudinal axis.

19. The needle holder according to claim 11, wherein the first jaw includes:
    a second outer edge surface extending in the proximal direction from the second proximal surface of the second protrusion, the second outer edge surface being transverse to the height direction; and
    a second guiding surface extending continuously from an inner edge of the second outer edge surface to the second wall surface so as to be transverse to the second outer edge surface and the second wall surface.

* * * * *